(12) United States Patent
Yamamoto et al.

(10) Patent No.: US 12,414,744 B2
(45) Date of Patent: Sep. 16, 2025

(54) IMAGING POSITION CORRECTION APPLICATION INTRODUCTION SUPPORT SYSTEM, AND IMAGING POSITION CORRECTION APPLICATION INTRODUCTION SUPPORT METHOD

(71) Applicant: Shimadzu Corporation, Kyoto (JP)

(72) Inventors: Junya Yamamoto, Kyoto (JP); Hiroshi Okumura, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 480 days.

(21) Appl. No.: 18/090,829

(22) Filed: Dec. 29, 2022

(65) Prior Publication Data

US 2023/0277142 A1    Sep. 7, 2023

(30) Foreign Application Priority Data

Mar. 2, 2022   (JP) ................. 2022-031745

(51) Int. Cl.
*A61B 6/04* (2006.01)
*A61B 6/00* (2006.01)
*G06T 7/00* (2017.01)

(52) U.S. Cl.
CPC .......... *A61B 6/0492* (2013.01); *A61B 6/5205* (2013.01); *G06T 7/0012* (2013.01); *G06T 2207/10116* (2013.01); *G06T 2207/30008* (2013.01)

(58) Field of Classification Search
CPC .......... A61B 6/032; A61B 6/587; A61B 6/03; A61B 6/02; A61B 6/027; A61B 6/04; A61B 6/5235; A61B 6/5211; A61B 6/584; A61B 6/547; A61B 5/70; A61N 5/1049; A61N 5/1048; A61N 2005/1052; A61N 2005/1063
See application file for complete search history.

(56) References Cited

U.S. PATENT DOCUMENTS

2018/0256134 A1   9/2018  Nakamura

FOREIGN PATENT DOCUMENTS

JP   2004313576 A  * 11/2004
JP   2018-143699 A    9/2018

* cited by examiner

*Primary Examiner* — Don K Wong
(74) *Attorney, Agent, or Firm* — Muir Patent Law, PLLC

(57) ABSTRACT

An imaging position correction application introduction support system is provided with a storage unit and a display unit. The imaging position correction application introduction support system is configured to cause the storage unit to store at least one of the number of times the imaging position correction application was used and a degree of correction when the relative position of the X-ray irradiation unit with respect to the specific site of the subject was corrected by the imaging position correction application, as the tentative use information on when the imaging position correction application is tentatively used. The display unit displays the information based on the tentative use information.

10 Claims, 5 Drawing Sheets

| | Application name | Number of uses | Degree of correction |
|---|---|---|---|
| 1 | Imaging position correction application 120a | 57 | Large |
| 2 | Imaging position correction application 120d | 43 | Large |
| 3 | Imaging position correction application 120b | 39 | Medium |

Introduction recommendation application

FIG.7

| Application name | Number of uses | Degree of correction |
|---|---|---|
| Imaging position correction application 120a | 57 | 21mm |
| Imaging position correction application 120b | 39 | 14mm |
| Imaging position correction application 120c | 11 | 5mm |
| Imaging position correction application 120d | 43 | 18mm |

IMAGING POSITION CORRECTION APPLICATION INTRODUCTION SUPPORT SYSTEM, AND IMAGING POSITION CORRECTION APPLICATION INTRODUCTION SUPPORT METHOD

CROSS-REFERENCE TO RELATED APPLICATIONS

The related application number JP2022-031745, entitled "Imaging Position Correction Application Introduction Support System and Imaging Position Correction Application Introduction Support Method," filed on Mar. 2, 2022, Junya Yamamoto, Hiroshi Okumura, upon which this patent application is based is hereby incorporated by reference.

BACKGROUND OF THE INVENTION

Field of the Invention

The present invention relates to an imaging position correction application introduction support system and an imaging position correction application introduction support method.

Description of the Related Art

Conventionally, there is known an imaging position correction application for easily positioning a radiation irradiation device of an X-ray imaging when capturing an X-ray image. Such an application is disclosed in, for example, Japanese Unexamined Patent Application Publication No. 2018-143699.

Japanese Unexamined Patent Application Publication No. 2018-143699 described above discloses an imaging position correction application configured to calculate a correction amount for a user to correct a position of a radiation irradiation device of an X-ray imaging device to a position where an imaging target appropriately appears and notify the calculated correction amount, when capturing an X-ray image.

Further, although not described in the above-described Japanese Unexamined Patent Application Publication No. 2018-143699, various imaging position correction applications corresponding to imaging sites are provided for an X-ray imaging system (X-ray imaging apparatus).

Here, although a user of an X-ray imaging system (X-ray imaging apparatus) considers introducing an imaging position correction application with a high need from among various imaging position correction applications, it is difficult for a provider or a user of the imaging position correction application to recognize in advance which imaging position correction application should be introduced prior to the actual introduction of the imaging position correction application. In such a case, even if it is an imaging position correction application with a high need for introduction for a user, the actual introduction may be deferred because of the reason that the provider or the user of the imaging position correction application couldn't recognize the need for the imaging position correction application prior to the actual introduction. Under the circumstance, there is a demand for an imaging position correction application introduction support system and an imaging position correction application introduction support method capable for a provider or a user of the imaging position correction application to recognize an imaging position correction application with a high need for introduction for a user prior to the actual introduction.

SUMMARY OF THE INVENTION

The present invention has been made to solve the above-described problems. One object of the present invention is to provide an imaging position correction application introduction support system and an imaging position correction application introduction support method capable for a provider or user of an imaging position correction application to recognize an imaging position correction application with a high need for introduction for the user prior to actual introduction.

An imaging position correction application introduction support system according to a first aspect of the present invention, includes:
- a storage unit configured to store tentative use information on when an imaging position correction application was tentatively used, as information to be used to recommend an actual introduction of the imaging position correction application tentatively used as an application for correcting a relative position of an X-ray irradiation unit for emitting X-rays with respect to a specific site of a subject when capturing an X-ray image of the specific site of the subject; and
- a display unit configured to display information based on the tentative use information stored in the storage unit,
- wherein the storage unit is configured to store, as the tentative use information, at least one of a number of times the imaging position correction application was used and a degree of correction when the relative position of the X-ray irradiation unit with respect to the specific site of the subject was corrected by the imaging position correction application.

An imaging position correction application introduction support method according to a second aspect of the present invention, includes:
- a storage step configured to cause the storage unit to store tentative use information on when an imaging position correction application was tentatively used, as information to be used to recommend an actual introduction of the imaging position correction application tentatively introduced as an application for correcting a relative position of an X-ray irradiation unit for emitting X-rays with respect to a specific site of a subject when capturing an X-ray image of the specific site of the subject; and
- a display step configured to display information based on the tentative use information stored in the storage unit;
- wherein the storage step includes a step configured to cause the storage to store, as the tentative use information, at least one of the number of times the imaging position correction application was used and a degree of correction when the relative position of the X-ray irradiation unit with respect to the specific site of the subject was corrected by the imaging position correction application.

In the imaging position correction application introduction support system according to the first aspect of the present invention and the imaging position correction application introduction support method according to the second aspect of the present invention, as the information used to recommend actual introduction of an imaging position correction application tentatively introduced, tentative use information on when the imaging position correction application was tentatively used is stored, and information based on the tentative use information is displayed. Then, as the tentative use information, at least one of the number of times the imaging position correction application was used and the degree of correction when the relative position of the X-ray irradiation unit with respect to a specific site of the subject was corrected by the imaging position correction application is stored in a storage unit. With this, in a case where the number of times the imaging position correction application was used is stored as the tentative use information, it is possible for the provider or the user of the imaging position correction application to recognize the imaging position correction application with a high use frequency when tentatively introduced and high possibility when actually introduced, by visually recognizing the information based on the tentative use information. As a result, it is possible to provide an imaging position correction application introduction support system and an imaging position correction application introduction support method capable for the provider or the user of the imaging position correction application to recognize the imaging position correction application with a high need for introduction for the user prior to the actual introduction. Further, in a case where the degree of correction when the relative position of the X-ray irradiation unit with respect to the specific site of the subject was corrected by the imaging position correction application is stored, as the tentative use information, the provider or the user of the imaging position correction application can recognize an imaging position correction application with a high degree of correction when tentatively introduced and with a significant effect when introduced actually, by visually recognizing the information based on the tentative use information. This enables to provide an imaging position correction application introduction support system and an imaging position correction application introduction support method capable for the provider or the user of the imaging position correction application to recognize the imaging position correction application with a high need for introduction for the user. As a result, it is possible to provide an imaging position correction application introduction support system and an imaging position correction application introduction support method capable for the provider or the user of the imaging position correction application to recognize an imaging position correction application with a high need for introduction for the user prior to the actual introduction.

BRIEF DESCRIPTION OF THE DRAWINGS

The preferred embodiments of the present invention are shown by way of example, and not limitation, in the accompanying figures.

FIG. 7 is a diagram showing one example of tentative use information displayed on a display unit.

DETAILED DESCRIPTION OF THE PREFERRED EMBODIMENTS

In the following paragraphs, some preferred embodiments of the invention will be described by way of example and not limitation. It should be understood based on this disclosure that various other modifications can be made by those skilled in the art based on these illustrated embodiments.

Hereinafter, some embodiments in which the present invention is embodied will be described with reference to the attached drawings.

First Embodiment

A configuration of an imaging position correction application introduction support system 100 according to a first embodiment will be described with reference to FIG. 1 to FIG. 4.

(General Configuration of System)

Figure 1:
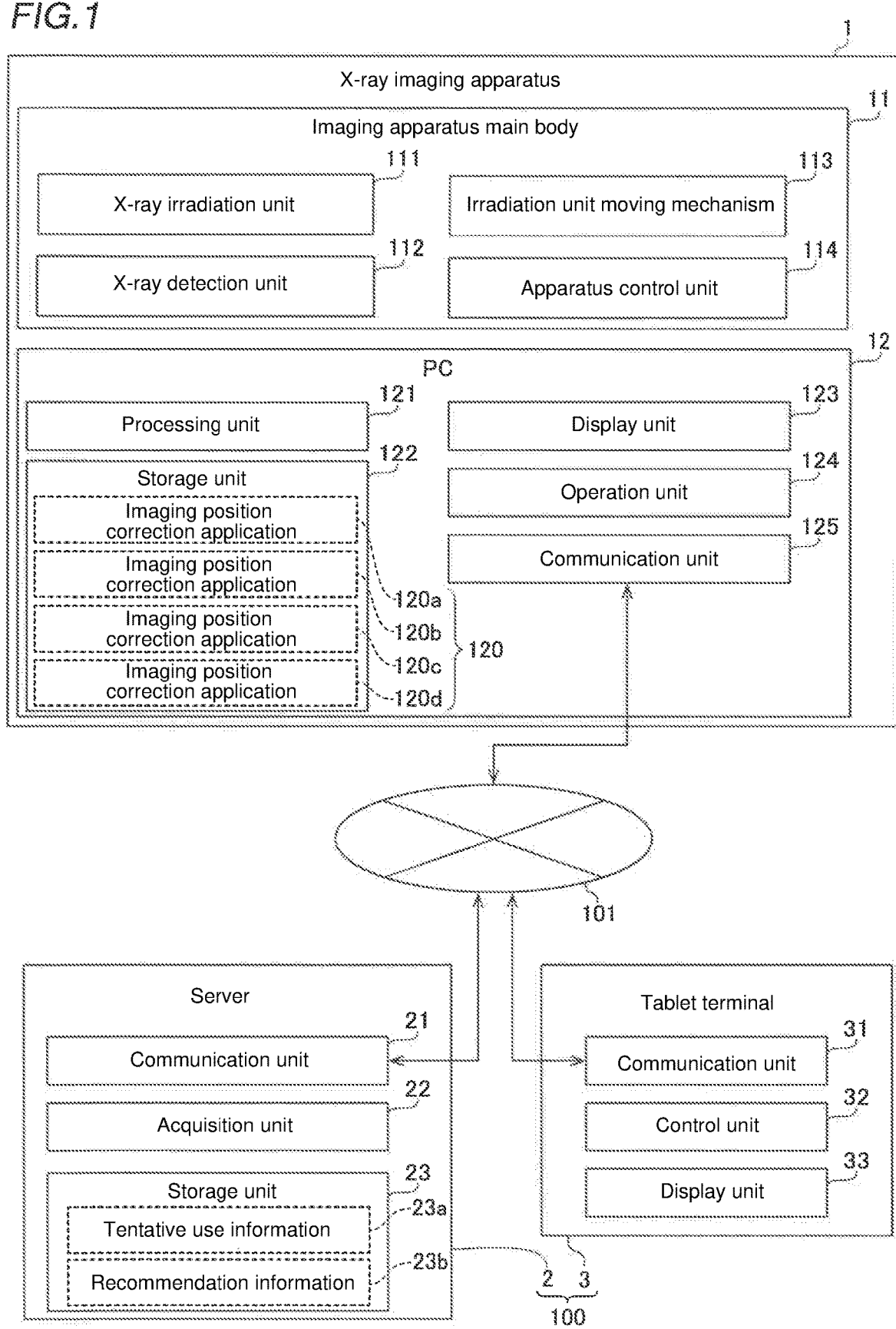
FIG. 1 is a schematic diagram showing an entire configuration of an imaging position correction application introduction support system according to a first embodiment of the present invention.
Figure 2:
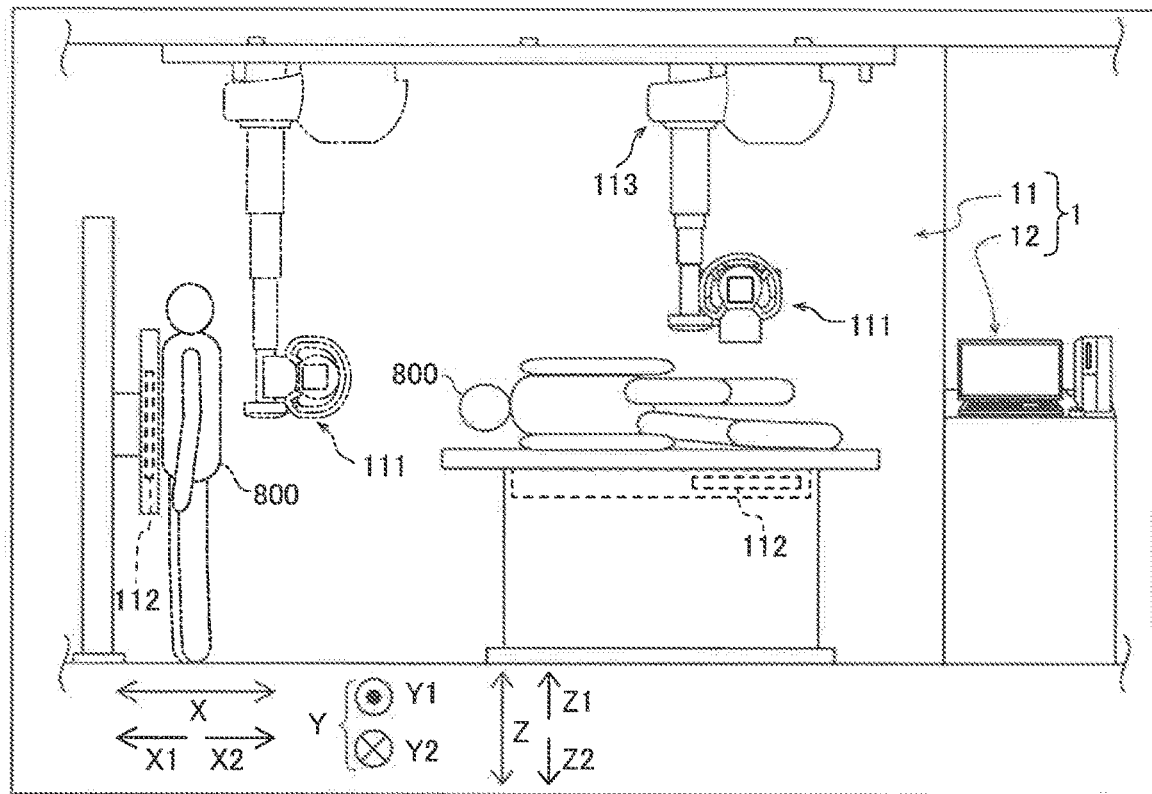
FIG. 2 is a schematic diagram showing a configuration of an X-ray imaging apparatus according to a first embodiment.

As shown in FIG. 1, the imaging position correction application introduction support system 100 is provided with a server 2 connected to the X-ray imaging apparatus 1 via a network 101, and a tablet terminal 3. The imaging position correction application introduction support system 100 is a system used to consider actual introduction of an imaging position correction application 120 (imaging position correction applications 120a, 120b, 120c, and 120d), which will be described later.

The X-ray imaging apparatus 1 is a device in which imaging position correction applications 120 (imaging position correction applications 120a, 120b, 120c, and 120d) are tentatively introduced, and an X-ray image 4 (see FIG. 3) of a subject 800 (see FIG. 2) is captured.

As shown in FIG. 1, the X-ray imaging apparatus 1 is provided with an imaging apparatus main body 11 and a PC12. Note that the PC12 is a console PC (Personal Computer) used for manipulation at the time of imaging by the imaging apparatus main body 11 and an analysis of the captured X-ray image 4, and the like.

The imaging apparatus main body 11 is provided with an X-ray irradiation unit 111, an X-ray detection unit 112, an irradiation unit moving mechanism 113, and an apparatus control unit 114.

The X-ray irradiation unit 111 is configured to irradiate the subject 800 with X-rays. The X-ray irradiation unit 111 is provided with an X-ray source (not shown) for irradiating the subject 800 with X-rays and a collimator (not shown) for adjusting the irradiation range of the X-rays.

The X-ray detection unit 112 is configured to detect the X-rays emitted from the X-ray irradiation unit 111 and transmitted through the subject 800. The X-ray detection unit 112 is, for example, an FPD (Flat Panel Detector) and detects the X-rays transmitted through the subject 800.

The irradiation unit moving mechanism 113 is configured to change the relative position of the X-ray irradiation unit 111 with respect to the subject 800 by moving the X-ray irradiation unit 111. In the X-ray imaging apparatus 1, the X-ray irradiation unit 111 is supported by being suspended from the ceiling by the irradiation unit moving mechanism 113. The X-ray irradiation unit 111 is movably supported in an imaging room by the irradiation unit moving mechanism 113. The irradiation unit moving mechanism 113 is provided with a motor and an electromagnetic brake (not shown) corresponding to each of the X-direction, the Y-direction, and the Z-direction. The X-ray irradiation unit 111 is configured to be movable by the irradiation unit moving mechanism 113 in each of the X-direction, the Y-direction, and the Z-direction. Further, the irradiation unit moving mechanism 113 is provided with an encoder (not shown) used to control the movements of the X-ray irradiation unit 111 corresponding to each of the X-direction, the Y-direction, and the Z-direction. Further, the irradiation unit moving mechanism 113 is provided with a potentiometer (not shown) corresponding to each of the X-direction, the Y-direction, and the Z-direction and is configured to be able to detect the position of the X-ray irradiation unit 111 in each of the X-direction, the Y-direction, and the Z-direction.

The apparatus control unit 114 includes a processor, such as, e.g., a CPU (Central Processing Unit) or an FPGA (Field-Programmable Gate Array). The apparatus control unit 114 is configured to control the entire imaging apparatus main body 11. Specifically, the apparatus control unit 114 is configured to perform control of X-ray irradiation by the X-ray irradiation unit 111, such as, e.g., starting and stopping the X-ray irradiation, control of the change of the X-ray irradiation range by the X-ray irradiation unit 111, control of the detection by the X-ray detection unit 112, control of the movements of the X-ray irradiation unit 111 by the irradiation unit moving mechanism 113, control of the movements of the top board, and the like.

Further, the apparatus control unit 114 is configured to receive the detection signal of encoders and potentiometers (not shown) included in the irradiation unit moving mechanism 113. Further, the apparatus control unit 114 is configured to control a motor (not shown) and an electromagnetic brake (not shown) equipped in the irradiation unit moving mechanism 113.

The PC12 is provided with a processing unit 121, a storage unit 122, a display unit 123, an operation unit 124, and a communication unit 125. The PC12 is communicatively coupled to the imaging apparatus main body 11 (apparatus control unit 114). Note that the PC12 may be integrally formed with the apparatus control unit 114.

The processing unit 121 includes a CPU, a GPU (Graphics Processing Unit), an ROM (Read Only Memory), and a RAM (Random Access Memory).

The storage unit 122 includes a storage device (internal storage), such as, e.g., an HDD (Hard Disk Drive) and an SSD (Solid State Drive).

The display unit 123 includes, for example, a liquid crystal display or an organic EL display. The operation unit 124 is a user interface for operating the PC12. The operation unit 124 includes, for example, a keyboard, a mouse, and the like. The display unit 123 may be provided with a touch panel as the operation unit 124.

The communication unit 125 is a communication interface. The PC 12 is configured to transmit tentative use information 23*a* to the server 2 by the communication unit 125 via the network 101.

To the X-ray imaging apparatus 1, imaging position correction applications 120*a*, 120*b*, 120*c*, and 120*d* are tentatively introduced as imaging position correction applications 120 which are application software for correcting the relative position of the X-ray irradiation unit 111 for emitting X-ray with respect to a specific site of a subject 800 when capturing an X-ray image 4 of the specific site of the subject 800. Note that the imaging position correction applications 120*a*, 120*b*, 120*c*, and 120*d* are examples of "a plurality of imaging position correction applications" as recited in claims.

Further, the imaging position correction application 120*a* is an imaging position correction application 120 for correcting the relative position of the X-ray irradiation unit 111 with respect to a knee of the subject 800 when capturing an X-ray image 4 of a knee (knee joint) of the subject 800. The imaging position correction application 120*a* is one example of the "knee imaging position correction application" recited in claims.

The imaging position correction applications 120*b*, 120*c*, and 120*d* each are, for example, an imaging position correction application 120 for correcting the relative position of the X-ray irradiation unit 111 with respect to each imaging target when capturing an X-ray image 4 of a chest, an elbow, and a waist, respectively.

The server 2 is configured to be connected to the X-ray imaging apparatus 1 via the network 101. The server 2 includes a communication unit 21, an acquisition unit 22, and a storage unit 23. Note that the acquisition unit 22 and the storage unit 23 of the server 2 are examples of the "acquisition unit" and the "storage unit" recited in claims, respectively.

The server 2 is configured to cause the storage unit 23 to store the tentative use information 23*a* acquired from the X-ray imaging apparatus 1 via the network 101 and acquire recommendation information 23*b* for recommending the introduction of the imaging position correction application 120 to the user, based on the tentative use information 23*a* stored in the storage unit 23. Further, the recommendation information 23*b* is stored in the storage unit 23.

The communication unit 21 of the server 2 is a communication interface. The acquisition unit 22 of the server 2 includes a processor, such as, e.g., a CPU, and a memory. The server 2 (acquisition unit 22) acquires the tentative use information 23*a* from the X-ray imaging apparatus 1 via the network 101 by the communication unit 21 and stores it in the storage unit 23.

The storage unit 23 of the server 2 includes a storage device (internal storage), such as, e.g., an HDD and an SSD. The storage unit 23 of the server 2 stores tentative use information 23*a* on when each of the imaging position correction applications 120*a*, 120*b*, 120*c*, and 120*d* was tentatively used, as information used to recommend the actual introduction of the imaging position correction applications 120*a*, 120*b*, 120*c*, and 120*d* tentatively introduced.

Note that the tentative use information 23*a* is stored in the storage unit 122 of the PC 12 temporarily or for a long period of time when each of the imaging position correction applications 120*a*, 120*b*, 120*c*, and 120*d* is tentatively used, in the X-ray imaging apparatus 1, and is stored in the storage unit 23 of the server 2 by being transmitted to the server 2 via the network 101.

The tentative use information 23*a* is stored, for example, as log information on each of the imaging position correction applications 120*a*, 120*b*, 120*c*, and 120*d*. In this case, the tentative use information 23*a* is stored in the storage unit 122 of the PC temporarily or for a long period of time by the imaging position correction applications 120*a*, 120*b*, 120*c*, and 120*d*, respectively. Alternatively, each tentative use information 23*a* of the imaging position correction applications 120*a*, 120*b*, 120*c*, and 120*d* may be collectively managed and stored by a dedicated application for storing the tentative use information 23*a*.

Further, the tentative use information 23*a* is stored in the storage unit 23 of the server 2 in real time, for example, during the use of each of the imaging position correction applications 120*a*, 120*b*, 120*c*, and 120*d*. Further, tentative use information 23*a* stored in the X-ray imaging apparatus 1 (storage unit 122) may be transmitted to the server 2 via the network 101 and stored in the storage unit 23 of the server 2 when each of the imaging position correction applications 120*a*, 120*b*, 120*c*, and 120*d* is started or terminated.

Further, in a case where the usage fee or the purchase fee of the imaging position correction application 120 is determined depending on the number of available functions included in the imaging position correction application 120, the extra cost can be reduced by limiting (disabling) less needed functions. Therefore, in a case where each of the imaging position correction applications 120*a*, 120*b*, 120*c*, and 120*d* has a plurality of correction functions, the imaging position correction application introduction support system 100 is configured to store tentative use information 23*a* (the number of uses and the degree of correction) for each correction function. In this way, the provider or the user of the imaging position correction application 120 can consider the actual introduction of the imaging position correction application 120 not only in the unit of the imaging position correction application 120 but also in the correcting function unit of the imaging position correction application 120.

Further, in a case where there is a mistake in imaging, such as, e.g., a mistake in setting the imaging site and a mistake in setting the imaging direction, when using each of the imaging position correction applications 120*a*, 120*b*, 120*c*, and 120*d*, the imaging position correction application introduction support system 100 may store presence or absence of the mistake in imaging, such as, e.g., the mistake in setting the imaging site and the mistake in setting the imaging direction, as the tentative use information 23*a*.

The imaging position correction application introduction support system 100 is configured to store, as tentative use information 23*a*, the number of times each of the imaging position correction applications 120*a*, 120*b*, 120*c*, and 120*d* was used, in the storage unit 23 of the server 2. Further, the imaging position correction application introduction support system 100 is configured to store, as the tentative use information 23*a*, the degree of correction when the relative position of the X-ray irradiation unit 111 with respect to the subject 800 was corrected, by each of the imaging position correction applications 120*a*, 120*b*, 120*c*, and 120*d*, respectively, in the storage unit 23 of the server 2. The degree of correction to be stored as the tentative use information 23*a* may be each value of the correction amount in all corrections performed within a time period during which it was tentatively introduced or within a predetermined time period, or may be a maximal value or an average value of the correction amounts of all corrections performed within a time period during which it was tentatively introduced or within a predetermined time period.

That is, the storage unit 23 of the server 2 is storing, as the tentative use information 23*a*, the number of times the imaging position correction application as a knee imaging position correction application 120*a* was used and the degree of correction when the relative position of the X-ray irradiation unit 111 with respect to the knee of the subject 800 was corrected by the imaging position correction application 120*a*.

The acquisition unit 22 of the server 2 is configured to acquire the recommendation information 23*b* including the information on the imaging position correction application 120 recommended to be actually introduced, as the information for recommending the actual introduction of the imaging position correction application 120 (imaging position correction applications 120*a*, 120*b*, 120*c*, and 120*d*) to the user, based on the tentative use information 23*a*.

In the first embodiment, the acquisition unit 22 determines the imaging position correction application 120 recommended to be actually introduced, based on the magnitude of the number of times each of imaging position correction applications 120*a*, 120*b*, 120*c*, and 120*d* was used and the magnitude of the degree of correction when the relative position of the X-ray irradiation unit 111 with respect to the specific site of the subject 800 was corrected by each of the imaging position correction applications 120*a*, 120*b*, 120*c*, and 120*d*.

In other words, the acquisition unit 22 determines the imaging position correction application 120*a* as the imaging position correction application 120 recommended to be actually introduced, based on the magnitude of the number of times the imaging position correction application 120*a* as a knee imaging position correction application was used and the magnitude of the degree of correction when the relative position of the X-ray irradiation unit 111 with respect to the knee of the subject 800 was corrected.

And, the acquisition unit 22 is configured to acquire the recommendation information 23*b* including the information on the imaging position correction application 120 recommended to be actually introduced, the recommendation information 26*b* being determined based on the magnitude of the number of times each of the imaging position correction applications 120*a*, 120*b*, 120*c*, and 120*d* was used, and the magnitude of the degree of correction when the relative position of the X-ray irradiation unit 111 with respect to the specific site of the subject 800 was corrected by each of the imaging position correction applications 120*a*, 120*b*, 120*c*, and 120*d*.

Further, the server 2 may be connected to a plurality of X-ray imaging apparatuses 1 via the network 101 to acquire the tentative use information 23*a* from each of the plurality of X-ray imaging apparatuses 1 and acquire the recommendation information 23*b* individually or collectively from each of the acquired tentative use information 23*a*. Further, the server 2 may be configured to be connected to a plurality of user's X-ray imaging apparatuses 1 via the network 101 to acquire the tentative use information 23*a* from each of the X-ray imaging apparatuses 1 of a plurality of users and acquire the recommendation information 23*b* from each acquired tentative use information 23*a* for each user.

The tablet terminal 3 is provided with a communication unit 31, a control unit 32, and a display unit 33. The tablet terminal 3 is, for example, a terminal owned by the provider of the imaging position correction application 120. The tablet terminal 3 is used when the provider of the imaging position correction application 120 recommends the introduction of the imaging position correction application 120 to a user.

The communication unit 31 is a communication interface. The tablet terminal 3 acquires the recommendation information 23*b* from the server 2 via the network 101 by the communication unit 31.

The control unit 32 is configured to control the entire tablet terminal 3. The control unit 32 controls the entire tablet terminal 3 based on the software installed on the terminal. Specifically, the control unit 32 is configured to perform control of communication using the communication unit 31, control of displaying the display unit 33, and the like.

The display unit 33 is configured to display the information based on the tentative use information 23*a* stored in the storage unit 23. The display unit 33 is, for example, a touch panel display including a liquid crystal display or an organic EL display. In the first embodiment, the display unit 33 is configured to display the recommendation information 23b as the information based on the tentative use information 23a.

(Imaging Position Correction)

When capturing an X-ray image 4, it is necessary to adjust the posture of the subject 800 and the position of the X-ray irradiation unit 111 so that the posture of the subject 800 and the position of the X-ray irradiation unit 111 are appropriate depending on the observation target site. Since the appropriate posture of the subject 800 and the appropriate position of the X-ray irradiation unit 111 differ depending on the observation target site, it is required to perform correction of the relative position of the X-ray irradiation unit 111 with respect to the observation target unit of the subject 800 by the corresponding imaging position correction application 120.

Figure 3:
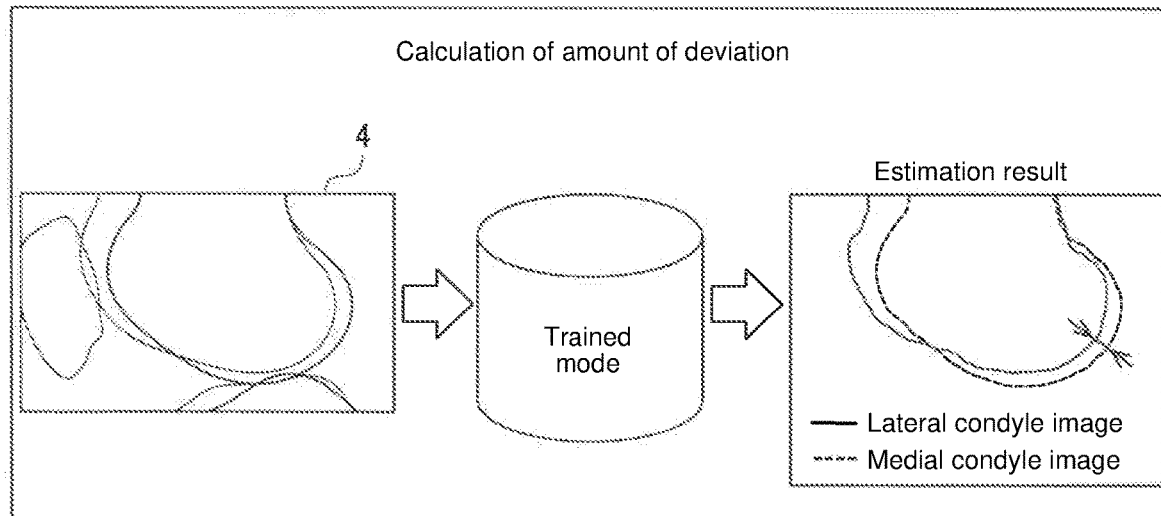
FIG. 3 is a diagram showing one example of the processing performed by an imaging position correction application.

For example, in the case of imaging a knee (knee joint), the imaging position correction application 120a is used. In the imaging position correction application 120a, as shown in FIG. 3, the outer edge of the medial condyle and the outer edge of the lateral condyle of the femoral bone are identified (estimated) from the X-ray image 4 by the segmentation processing by a trained model. Then, based on the outer edge of the medial condyle and the outer edge of the lateral condyle identified (estimated) from the X-ray image 4, the deviation between the outer edge of the medial condyle and the outer edge of the lateral condyle of the femoral bone (the deviation amount and the deviation direction) is calculated. Note that the X-ray image 4 used for calculating the deviation may be an image captured with substantially the same radiation amount as an image used for the actual diagnosis, or may be an image captured with a less radiation amount than an image used for the actual diagnosis.

In the imaging position correction application 120a, based on the calculated deviation (the deviation amount and the deviation direction) between the outer edge of the medial condyle and the outer edge of the lateral condyle, position correction information for correcting the relative position of the X-ray irradiation unit 111 with respect to the knee of the subject 800 is calculated to a position where the X-ray image 4 in which the outer edge of the medial condyle and the outer edge of the lateral condyle overlap each other can be imaged. The imaging position correction application 120a has a function of automatically correcting the position of the X-ray irradiation unit 111 based on the calculated position correction information. With this, it is possible to capture the X-ray image 4 capable of accurately identifying diseases occurring around the knee joint, such as, e.g., disruptive bone cartilage inflammation and osteoarthritis.

As described above, the correction by the imaging position correction applications 120 (the imaging position correction application 120a, 120b, 120c, and 120d) may be performed based on the X-ray image 4 or may be performed based on a camera image acquired by imaging visible light or the like. Further, the correction by the imaging position correction application 120 may be performed based on both the X-ray image 4 and the camera image acquired by imaging visible light or the like. That is, in the imaging position correction application introduction support system 100, the imaging position correction application 120 tentatively introduced and considered for actual introduction may be an imaging position correction application 120 that performs corrections in any manner.

In the imaging position correction application 120 (imaging position correction application 120a, 120b, 120c, and 120d), in a case where the relative position of the X-ray irradiation unit 111 with respect to the observation target site of the subject 800 is not appropriate or the like, it is determined that a correction by the imaging position correction application 120 is required. That is, the case where the degree of correction when performing the correction by the imaging position correction application 120 is large is considered to be a case in which the positional matching of the relative position of the X-ray irradiation unit 111 with respect to the observation target site of the subject 800 is insufficient.

(Acquisition of Recommendation Information)

In the first embodiment, the acquisition unit 22 is configured to, based on the magnitude of the number of times each of the imaging position correction applications 120a, 120b, 120c, and 120d was used, select an imaging position correction application 120 recommended to be actually introduced from among the imaging position correction applications 120a, 120b, 120c, and 120d and acquire the recommendation information 23b including the information on the selected imaging position correction application 120 recommended to be actually introduced.

Specifically, the acquisition unit 22 selects the imaging position correction application 120 recommended to be actually introduced, from among the imaging position correction applications 120a, 120b, and 120c, based on the comparison of the number of times each of the imaging position correction applications 120a, 120b, 120c, and 120d was used with the predetermined threshold of the number of uses, and the ranking of the imaging position correction applications 120 based on the number of times each of the imaging position correction applications 120a, 120b, 120c, and 120d was used. The acquisition unit 22 is configured to acquire the recommendation information 23b including the information on the imaging position correction application 120 recommended to be actually introduced selected from among the imaging position correction applications 120a, 120b, 120c, and 120d.

Note that the predetermined threshold of the number of uses may be set by the provider of the imaging position correction application introduction support system 100 or may be changed (set) according to the user's request. By setting the threshold of the number of uses, the acquisition unit 22 can exclude an imaging position correction application 120 with the number of uses less than the predetermined threshold of the number of uses from among the tentatively used imaging position correction applications 120. The ranking based on the number of times the imaging position correction application 120 was used allows the acquisition unit 22 to acquire the priority order of the imaging position correction application 120 recommended to be actually introduced.

Further, the acquisition unit 22 is configured to select an imaging position correction application 120 recommended to be actually introduced, from among the imaging position correction application 120a, 120b, 120c, and 120d, based on the degree of correction when the relative position of the X-ray irradiation unit 111 with respect to the specific site of the subject 800 was corrected by each of the imaging position correction applications 120a, 120b, 120c, and 120d and the predetermined threshold of the degree of correction, and acquire the recommendation information 23b including the information on the selected imaging position correction application 120 recommended to be actually introduced.

The predetermined threshold of the degree of correction may be set by the provider of the imaging position correction application introduction support system 100 or may be changed (set) according to the user's request. For example, the predetermined threshold of the degree of correction may be set according to the image (failed image) that needs to be re-taken and the reference determined by the user.

Figures 4, 5:
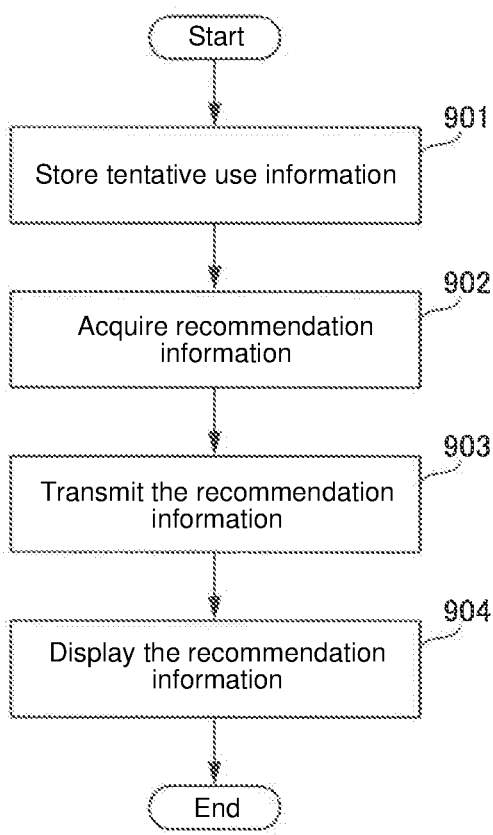
FIG. 4 is a diagram showing one example of recommendation information displayed on a display unit of a tablet terminal in the first embodiment.
FIG. 5 is a flowchart showing one example of the processing performed by an imaging position correction application introduction support system.

In the first embodiment, as shown in FIG. 4, on the display unit 33 of the tablet terminal 3, as the recommendation information 23b, the application name, the number of uses, and the degree of correction of each of the imaging position correction applications 120 recommended to be actually introduced are displayed. In FIG. 4, an example is shown in which the recommendation information 23b in which the imaging position correction applications 120 with the higher number of uses and the higher degree of correction among the imaging position correction applications 120a, 120b, 120c, and 120d are shown as the imaging position correction applications 120 recommended to be actually introduced.

Note that imaging position correction application introduction support system 100 (X-ray imaging apparatus 1) can also display the recommendation information 23b on the display unit 123 of the X-ray imaging apparatus 1 by transmitting the recommendation information 23b from the server 2 to the X-ray imaging apparatus 1 via the network 101.

(Processing Flow of Imaging Position Correction Application Introduction Support System)

Next, the processing flow in acquiring the tentative use information 23a and the recommendation information 23b by the imaging position correction application introduction support system 100 according to the first embodiment will be described with reference to FIG. 5.

In Step 901, the tentative use information 23a is stored. In Step 901, as the information used to recommend the actual introduction of the tentatively used imaging correction application 120, the tentative use information 23a acquired when the imaging position correction application 120 was tentatively used is stored in the storage unit 23. Note that Step 901 is one example of the "storage step" recited in claims.

In Step 901, as described above, as the tentative use information 23a, the number of times the imaging position correction application 120 was tentatively used and the degree of correction when the relative position of the X-ray irradiation unit 111 with respect to the specific site of the subject 800 was corrected by the tentatively used imaging position correction application 120 are stored in the storage unit 23.

In Step 902, the recommendation information 23b is acquired. In Step 902, based on the tentative use information 23a, as the information for recommending the actual introduction of the imaging position correction application 120 to the user, the recommendation information 23b including the information on the imaging position correction application 120 recommended to be actually introduced is acquired by the acquisition unit 22 of the server 2. Note that the transition from Step 901 to Step 902 may be performed after the completion of Step 901, or when the server 2 accepts the operation for acquiring the recommendation information 23b after completion of Step 901, the processing step may proceed to Step 902. Then, after completion of Step 902, the processing step proceeds to Step 903.

In Step 903, the recommendation information 23b is transmitted. In Step 903, the recommendation information 23b acquired by the acquisition unit 22 of the server 2 in Step 902 is transmitted from the server 2 to the tablet terminal 3 via the network 101. After completing Step 903, the processing step proceeds to Step 904.

In Step 904, the recommendation information 23b is displayed. In Step 904, as the information based on the tentative use information 23a stored in Step 901, the recommendation information 23b transmitted from the server 2 in Step 903 is displayed on the display unit 33 (see FIG. 4). Note that Step 904 is one example of the "display step" recited in claims.

Note that in Step 903, it may be configured such that the recommendation information 23b is transmitted to the X-ray imaging apparatus 1, and in Step 904, the recommendation information 23b is displayed on the display unit 123 of the X-ray imaging apparatus 1.

Effects of First Embodiment

In the first embodiment, the following effects can be obtained.

In the first embodiment, the information (recommendation information 23b) based on the tentative use information 23a is stored as the information used to recommend the actual introduction of the tentatively used imaging position correction applications 120 (imaging position correction applications 120a, 120b, 120c, and 120d), and the information (recommendation information 23b) based on the tentative use information 23a is displayed.

Then, as the tentative use information 23a, the number of times the imaging position correction application 120 was used, and the degree of correction when the relative position of the X-ray irradiation unit 111 with respect to the specific site of the subject 800 was corrected by the imaging position correction application 120 are stored in the storage unit 23. With this, the number of times the imaging position correction application 120 was used is stored as the tentative use information 23a. Therefore, the provider or the user of the imaging position correction application 120 can recognize the imaging position correction application 120 with the higher frequency of uses when tentatively introduced and the higher possibility of uses when actually introduced by visually recognizing the information (recommendation information 23b) based on the tentative use information 23a. As a consequence, the provider or the user of the imaging position correction application 120 can recognize the imaging position correction application 120 with a high need for introduction for the user prior to the actual introduction.

Further, as the tentative use information 23a, the degree of correction when the relative position of the X-ray irradiation unit 111 with respect to the specific site of the subject 800 was corrected by the imaging position correction application 120 is stored. Therefore, the provider or user of the imaging position correction application 120 can recognize the imaging position correction application 120 with a higher degree of correction when tentatively introduced and a more significant effect when tentatively introduced by visually recognizing the information (recommendation information 23b) based on tentative use information 23a. With this, the provider or the user of the imaging position correction application 120 can recognize the imaging position correction application 120 with a high need for introduction for the user prior to the actual introduction.

Consequently, the provider or the user of the imaging position correction application 120 can recognize the imaging position correction application 120 with the higher possibility of usage when actually introduced and a more significant effect when actually introduced, by visually recognizing the information (recommendation information 23b) based on the tentative use information 23a. This allows the provider or the user of the imaging position correction application 120 to recognize the imaging position correction application 120 with a higher need for introduction for the user prior to the actual introduction.

Further, in the imaging position correction application introduction support system 100 according to the first embodiment, the following further effects can be obtained by configuring as follows.

In the first embodiment, the acquisition unit 22 of the server 2 acquires, based on the tentative use information 23a, the recommendation information 23b including the information on the imaging position correction application 120 recommended to be actually introduced, as the information for recommending the actual introduction of the imaging position correction application 120 (imaging position correction applications 120a, 120b, 120c, and 120d) for the user. This allows the provider or the user of the imaging position correction application 120 to acquire the recommendation information 23b including the information on the imaging position correction application 120 recommended to be actually introduced, by the acquisition unit 22 of the server 2, without carefully reviewing the tentative use information 23a.

Consequently, the provider of the imaging position correction application 120 can use the recommendation information 23b acquired by the acquisition unit 22 of the server 2, including the information on the imaging position correction application 120 recommended to be actually introduced, when proposing the introduction of the imaging position correction application 120 to the user. With this, as compared with a case in which the introduction of the imaging position correction application 120 is proposed to a user by using only the tentative use information 23a, the provider can easily propose the introduction of the imaging position correction application 120 to a user.

Further, the display unit 33 displays, as the information based on the tentative use information 23a, the recommendation information 23b including the information on the imaging position correction applications 120 recommended to be actually introduced. With this, the user and the provider of the imaging position correction application 120 can recognize the imaging position correction application 120 with a higher need for introduction by visually recognizing the recommendation information 23b displayed on the display unit 33.

Further, in the first embodiment, the acquisition unit 22 is configured to acquire the recommendation information 23b including the information on the imaging position correction application 120 recommended to be actually introduced, determining the imaging position correction application 120 recommended to be actually introduced, based on the magnitude of the number of times each of the imaging position correction applications 120a, 120b, 120c, and 120d was used, and the magnitude of the degree of correction when the relative position of the X-ray irradiation unit 111 with respect to the specific site of the subject 800 was corrected by each of the imaging position correction applications 120a, 120b, 120c, and 120d.

As a result, the user and the provider of the imaging position correction application 120 can recognize the imaging position correction application 120 with a higher possibility of use when actually introduced and a higher need for introduction by the recommendation information 23b acquired by the acquisition unit 22, based on the magnitude of the number of times each of the imaging position correction applications 120a, 120b, 120c, and 120d was used.

Further, the user or the provider of the imaging position correction application 120 can recognize the imaging position correction application with a more significant effect when actually introduced and a higher need for introduction by the recommendation information 23b acquired by the acquisition unit 22, based on the magnitude of the degree of correction when the relative position of the X-ray irradiation unit 111 with respect to the specific site of the subject 800 was corrected.

As a consequence, the user and the provider of the imaging position correction application 120 can recognize the imaging position correction application 120 with a higher possibility of use when actually introduced, a more significant effect when actually introduced, and a higher need for introduction, from the recommendation information 23b.

Further, in the first embodiment, the acquisition unit 22 is configured to select the imaging position correction application 120 recommended to be actually introduced from among the imaging position correction applications 120a, 120b, 120c, and 120d, based on the magnitude of the number of times each of the imaging position correction applications 120a, 120b, 120c, and 120d was used, and acquire the recommendation information 23b including the information on the selected imaging position correction application 120 recommended to be actually introduced.

With this, the user and the provider of the imaging position correction application 120 can recognize the imaging position correction application 120 with a higher possibility of use when actually introduced and a higher need for introduction by the recommendation information 23b acquired based on the magnitude of the number of uses by the acquisition unit 22 from among the tentatively used imaging position correction applications 120a, 120b, 120c and 120d.

Further, in the first embodiment, the acquisition unit 22 is configured to acquire the recommendation information 23b including information on the imaging position correction application 120 recommended to be actually introduced selected from among the imaging position correction applications 120a, 120b, 120c and 120d, based on the comparison between the number of times each of the imaging position correction applications 120a, 120b, 120c, and 120d was used and the predetermined threshold of the number of uses and the ranking of the imaging position correction applications 120 based on the number of times each of the imaging position correction applications 120a, 120b, 120c, and 120d was used.

With this, the acquisition unit 22 can acquire the recommendation information 23b including the information on the imaging position correction application 120 with a higher usage possibility when actually introduced and higher introduction necessity from among the tentatively used imaging position correction applications 120a, 120b, 120c, and 120d, by selecting the imaging position correction application 120 used over a predetermined threshold of the number of uses as an imaging position correction application 120 recommended to be actually introduced.

Further, by selecting the imaging position correction application 120 recommended to be actually introduced with a higher ranking based on the number of times each of the imaging position correction applications 120a, 120b, 120c, and 120d was used, the recommendation information 23b including the information on the imaging position correction application 120 with higher usage possibility when actually introduced and higher introduction necessity can be acquired from among the tentatively used imaging position correction applications 120a, 120b, 120c, and 120d.

As a consequence, the acquisition unit 22 can acquire the recommendation information 23b including the information on the imaging position correction application 120 used over a predetermined threshold of the number of uses with a higher ranking based on the number of uses and higher usage possibility when actually introduced, from among the tentatively used imaging position correction application 120a, 120b, 120c, and 120d.

Further, in the first embodiment, the acquisition unit 22 is configured to acquire the recommendation information 23b including the information on the selected imaging position correction application 120 recommended to be actually introduced, from among the imaging position correction applications 120a, 120b, 120c, and 120d, based on the degree of correction when the relative position of the X-ray irradiation unit 111 with respect to the specific site of the subject 800 was corrected by each of the imaging position correction applications 120a, 120b, 120c, and 120d and the predetermined threshold of the degree of correction.

With this, the acquisition unit 22 can acquire the recommendation information 23b including the imaging position correction application 120 with a more significant effect when actually introduced and higher introduction necessity, from among the tentatively used imaging position correction applications 120a, 120b, 120c, and 120d, by selecting the imaging position correction application 120 that performs correction over a predetermined threshold of the degree of correction as an imaging position correction application 120 recommended to be actually introduced.

Further, in the first embodiment, the acquisition unit 22 determines the imaging position correction application 120a as an imaging position correction application 120 recommended to be actually introduced, based on the magnitude of the number of times the imaging position correction application 120a as a knee imaging position correction application was used and the magnitude of the degree of correction when the relative position of the X-ray irradiation unit 111 with respect to the knee of the subject 800 was corrected by the imaging position correction application 120. With this, in a case where the imaging position correction application 120a that is the tentatively used imaging position correction application is higher in the frequency of use when actually introduced and higher in possibility of uses when actually introduced, the information on the imaging position correction application 120a is included in the recommendation information 23b.

Further, in a case where the imaging position correction application 120a that is the tentatively introduced knee imaging position correction application was significant in the degree of correction when tentatively introduced and large in the effect when actually introduced, the information on the imaging position correction application 120a is included in the recommendation information 23b.

As a consequence, in a case where the imaging position correction application 120a that is the tentatively introduced knee imaging position correction application is the imaging position correction application 120 with high usage possibility when actually introduced and with a significant effect when actually introduced, the user and the provider of the imaging position correction application 120 can recognize that the imaging position correction application 120a is an imaging position correction application 12 with a high need for introduction, from the recommendation information 23b.

Further, in the first embodiment, the server 2 is configured to be connected to the X-ray imaging apparatus 1 via the network 101. The server 2 is configured to record the tentative use information 23a acquired from the X-ray irradiation unit 1 in the storage unit 23 via the network 101 and acquire the recommendation information 23b for recommending the introduction of the imaging position correction application 120 to the user, based on the tentative use information 23a stored in the storage unit 23.

With this, the provider of the imaging position correction application 120 can acquire the recommendation information 23b based on the tentative use information 23a acquired from the X-ray imaging apparatus 1, by accessing the server 2 via the network 101. Consequently, the provider of the imaging position correction application 120 can acquire the recommendation information 23b based on the tentative use information 23a without going to the location of the X-ray imaging apparatus 1 and propose the imaging position correction application 120 recommended to be actually introduced based on the recommendation information 23b to the user.

Second Embodiment

Figure 6:
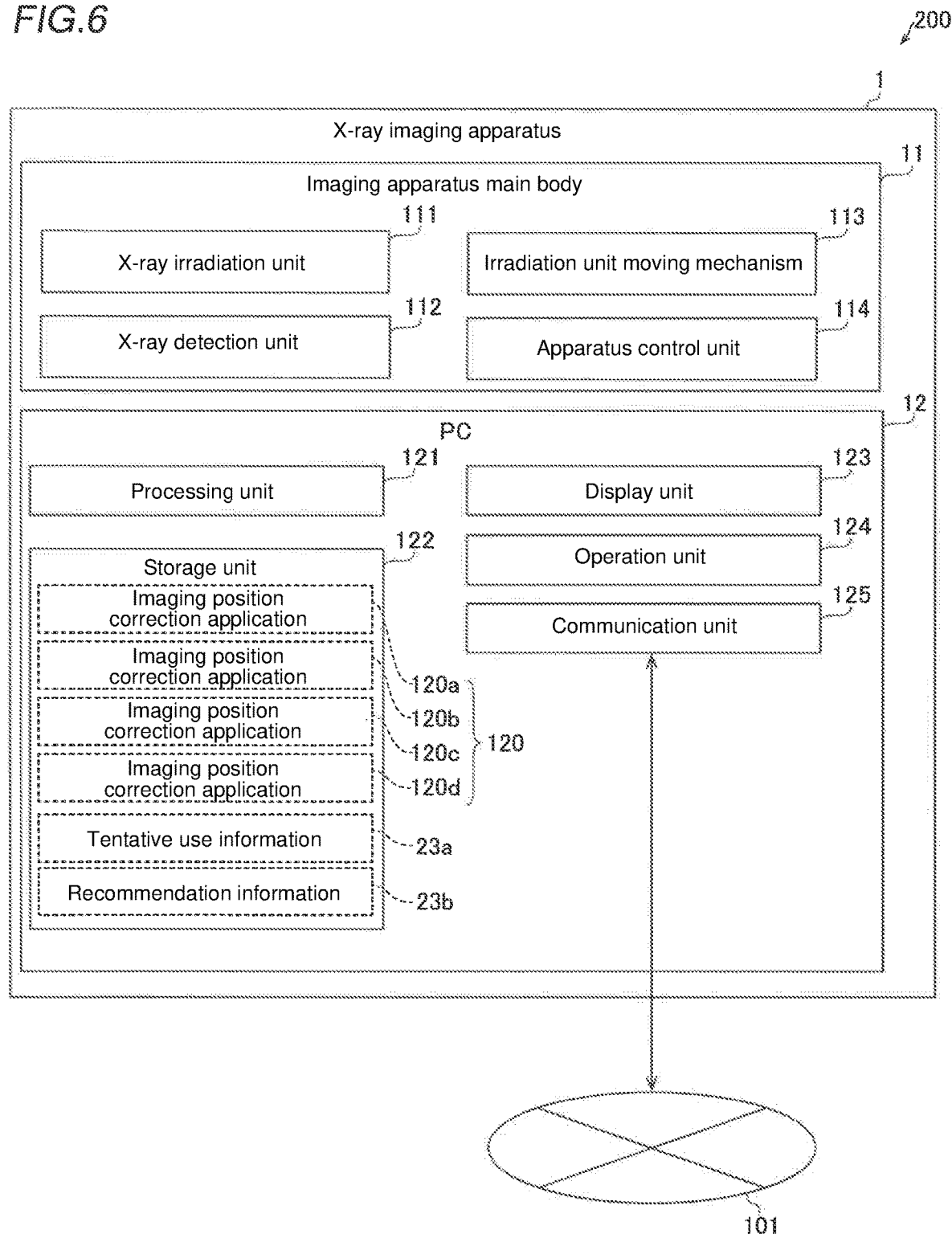
FIG. 6 is a schematic diagram showing an entire configuration of an imaging position correction application introduction support system according to a second embodiment of the present invention.

With reference to FIG. 6, the configuration of the imaging position correction application introduction support system 200 according to a second embodiment will be described. In the drawings, the same component as that of the first embodiment will be assigned by the same reference numeral.

In the imaging position correction application introduction support system 200 according to the second embodiment, the processing unit 121 in the PC 12 of the X-ray imaging apparatus 1 is configured to process the imaging position correction applications 120 (imaging position correction applications 120a, 120b, 120c, and 120d) and acquire the recommendation information 23b. Note that the processing unit 121 is one example of the "acquisition unit" and the "processing unit" recited in claims.

In the second embodiment, the processing unit 121 of the X-ray imaging apparatus 1 is configured to record the tentative use information 23a in the storage unit 122 and acquire the recommendation information 23b for recommending the actual introduction of the imaging position correction application 120 to the user based on the tentative use information 23a stored in the storage unit 122. The recommendation information 23b is stored in the storage unit 122. The processing unit 121 is configured to display the acquired recommendation information 23b on the display unit 123. Note that the X-ray imaging apparatus 1 may transmit the tentative use information 23a and the recommendation information 23b to an external device, such as, e.g., a tablet terminal 3 (see FIG. 1), via the network 101.

The rest of the configuration of the second embodiment is the same as that of the first embodiment.

Effects of Second Embodiment

In the second embodiment, the following effects can be obtained.

In the second embodiment, in the same manner as in the first embodiment described above, it is possible to provide an imaging position correction application introduction support system 200 capable for the provider or the user of the imaging position correction application 120 to recognize the imaging position correction application 120 with a high need for introduction for the user prior to the actual introduction.

Further, in the imaging position correction application introduction support system 200 according to the second embodiment, the following advantages can be further obtained by the following configuring.

In the second embodiment, the processing unit 121 of the X-ray imaging apparatus 1 is configured to cause the storage unit 122 to store the tentative use information 23a in the storage unit 122 and acquire the recommendation information 23b for recommending the actual introduction of the imaging position correction application 120 to the user, based on the tentative use information 23a stored in the storage unit 122. The processing unit 121 is configured to display the acquired recommendation information 23b on the display unit 123.

With this, in the X-ray imaging apparatus 1, since the tentative use information 23a is stored, and the recommendation information 23b is acquired, the imaging position correction application 120 with a high need for introduction for the user can be recognized prior to the actual introduction without connecting to the external network 101.

Other effects of the second embodiment are the same as those of the first embodiment.

Modified Embodiments

It should be understood that the embodiments disclosed here are examples in all respects and are not restrictive. The scope of the present invention is shown by claims rather than the descriptions of the embodiments described above, and includes all changes (modifications) within the meaning and the scope equivalent to the claims.

For example, in the first and second embodiments described above, an example is shown in which the recommendation information 23b is displayed as the information based on the tentative use information 23a, but the present invention is not limited thereto. In the present invention, as shown in FIG. 7, the tentative use information 23a may be displayed on the display unit 33 of the tablet terminal 3. Further, the tablet terminal 3 may be configured such that the tentative use information 23a and the recommendation information 23b can be displayed simultaneously or displayed in a switched manner. Further, the tentative use information 23a may be displayed on the display unit 123 (see FIG. 1) of the X-ray imaging apparatus 1.

Further, in the first and second embodiments, an example is shown in which the recommendation information 23b is acquired by the acquisition unit 22 and the processing unit 121, respectively, but the present invention is not limited thereto. In the present invention, the provider or the user may consider the imaging position correction application recommended to be actually introduced by visually recognizing the tentative use information displayed on the display unit.

Further, in the first and second embodiments described above, an example is shown in which the imaging position correction application introduction support system 100 stores, as the tentative use information 23a, the number of times the imaging position correction application 120 was used and the degree of correction when the relative position of the X-ray irradiation unit 111 with respect to the specific site of the subject 800 was corrected by the imaging position correction application 120 in the storage unit 23, but the present invention is not limited thereto. In the present invention, it may be configured such that the imaging position correction application introduction support system causes the storage unit to store, as the tentative use information, only one of the number of times the imaging position correction application was used and the degree of correction when the relative position of the X-ray irradiation unit with respect to the specific site of the subject was corrected by the imaging position correction application.

Further, in the first and second embodiments 1 described above, an example is shown in which the acquisition unit 22 determined the imaging position correction application 120 for recommending the actual introduction based on the magnitude of the number of times the imaging position correction application was used 120 and the magnitude of the degree of correction when the relative position of the X-ray irradiation unit 111 with respect to the specific site of the subject 800 was corrected by the imaging position correction application 120 and acquire the recommendation information 23b including the information on the determined imaging position correction application 120 recommended to be actually introduced, but the present invention is not limited.

In the present invention, it may be configured such that the acquisition unit determines the imaging position correction application recommended to be actually introduced based on only one of the magnitude of the number of times the imaging position correction application was used and the magnitude of the degree of correction when the relative position of the X-ray irradiation unit with respect to the specific site of the subject was corrected.

Further, in the first and second embodiments described above, an example is shown in which the acquisition unit 22 selects the imaging position correction application 120 recommended to be actually introduced from among the imaging position correction applications 120a, 120b, 120c, 120d, based on the magnitude of the number of times the imaging position correction application 120 was used and acquires the recommendation information 23b including the selected imaging position correction application 120 recommended to be actually introduced, but the present invention is not limited thereto.

The present invention may be used when tentatively introducing one imaging position correction application. In this situation, it is determined whether to recommend the introduction of the tentatively used imaging position correction application based on the magnitude of the number of times the imaging position correction application was used.

Further, in the first and second embodiments described above, an example is shown in which the acquisition unit 22 selects the imaging position correction application recommended to be actually introduced 120a, 120b, 120c, and 120d based on the comparison between the number of times each of the imaging position correction applications 120a, 120b, 120c, and 120d was used and a predetermined threshold of the number of uses, and the ranking of the imaging position correction application 120 based on the number of times each of the imaging position correction applications 120a, 120b, 120c, and 120d was used, and acquires the recommendation information 23b including the information on the selected imaging position correction application 120 recommended to be actually introduced, but the present invention is not limited thereto.

In the present invention, it may be configured such that the acquisition unit selects the imaging position correction application recommended to be actually introduced from among a plurality of imaging position correction applications, based on only one of the comparison between the number of times each of a plurality of imaging position correction applications was used and a predetermined threshold of the number of uses, and the ranking of the imaging position correction application based on the number of times each of the plurality of imaging position correction applications was used.

Further, in the first and second embodiments described above, an example is shown in which the acquisition unit 22 selects the imaging position correction application recommended to be actually introduced from among the imaging position correction applications 120a, 120b, 120c, and 120d based on the degree of correction when the relative position of the X-ray irradiation unit 111 with respect to the specific site of the subject 800 was corrected by the imaging position correction application 120 and the predetermined threshold of the degree of correction, and acquires the recommendation information 23b including the information on the selected actual introduced recommended imaging position correction application 120, but the present invention is not limited thereto.

The present invention may be used when tentatively introducing one imaging position correction application. In this case, whether to recommend the introduction of the tentatively used imaging position correction application is determined by the imaging position correction application, based on the degree of correction when the relative position of the X-ray imaging unit with respect to the specific site of the subject was corrected and the predetermined threshold of the degree of correction.

Further, in the second embodiment, an example is shown in which the tentative use information 23a is recorded in the storage unit 122 of the PC 12 of the X-ray imaging apparatus 1, but the present invention is not limited thereto. In the present invention, in the imaging position correction application introduction support system, the tentative use information may be stored in a storage unit, such as, e.g., a memory provided on the imaging apparatus main body 11 (see FIG. 1) of the X-ray imaging apparatus 1.

Further, in the first and second embodiments described above, an example is shown in which the tentative use information 23a of the imaging position correction application tentatively introduced into the ceiling-suspended X-ray imaging apparatus 1 and the recommendation information 23b are acquired, but the present invention is not limited thereto. In the present invention, the tentative use information on the imaging position correction application tentatively introduced to the X-ray fluoroscopic imaging table (fluoroscopic table) and the recommendation information may be acquired.

Further, in the first and second embodiments described above, for convenience of explanation, the processing (processing of the acquiring tentative use information 23a and the recommendation information 23b) in the imaging position correction application support system according to the present invention is described using a flow-driven flowchart that sequentially performs processing along the processing flow, but the present invention is not limited thereto.

In the present invention, the processing in the imaging position correction application introduction support system may be performed by event-driven processing (event-driven type) that executes processing on an event-by-event basis. In this case, the processing may be performed in a complete event-driven fashion or in combination of event-driven type processing and flow-driven type processing.

[Aspects]

It will be understood by those skilled in the art that the above-described exemplary embodiments are concrete examples of the following aspects.

(Item 1)

An imaging position correction application introduction support system, comprising:
 a storage unit configured to store tentative use information on when an imaging position correction application was tentatively used, as information to be used to recommend an actual introduction of the imaging position correction application tentatively used as an application for correcting a relative position of an X-ray irradiation unit for emitting X-rays with respect to a specific site of a subject when capturing an X-ray image of the specific site of the subject; and
 a display unit configured to display information based on the tentative use information stored in the storage unit,
 wherein the storage unit is configured to store, as the tentative use information, at least one of a number of times the imaging position correction application was used and a degree of correction when the relative position of the X-ray irradiation unit with respect to the specific site of the subject was corrected by the imaging position correction application.

(Item 2)

The imaging position correction application introduction support system as recited the above-described Item 1, further comprising:
 an acquisition unit configured to acquire, as the information to be used to recommend the actual introduction of the imaging position correction application to a user, recommendation information including information on the imaging position correction application recommended to be actually introduced, based on the tentative use information,
 wherein the display unit is configured to display the recommendation information as information based on the tentative use information.

(Item 3)

The imaging position correction application introduction support system as recited in the above-described Item 2,
 wherein the acquisition unit is configured to
 determine the imaging position correction application recommended to be actually introduced, based on at least one of magnitude of the number of times the imaging position correction application was used, the magnitude of the number of times being stored in the storage unit as the tentative use information, and magnitude of a degree of correction when the relative position of the X-ray irradiation unit with respect to the specific site of the subject was corrected by the imaging position correction application, the degree of correction being stored in the storage unit as the tentative use information, and
 acquire the recommendation information including information on the determined imaging position correction application recommended to be actually introduced.

(Item 4)

The imaging position correction application introduction support system as recited in the above-described Item 3,
 wherein the storage unit stores at least the number of times the imaging position correction application was used as the tentative use information, and
 wherein the acquisition unit is configured to
 select the imaging position correction application recommended to be actually introduced from a plurality of imaging position correction applications, based on the magnitude of the number of times the imaging position correction application was used, the number of times being stored in the storage unit as the tentative use information, and
 acquire the recommendation information including information on the selected imaging position correction application recommended to be actually introduced.

(Item 5)
The imaging position correction application introduction support system as recited in the above-described Item 4,
wherein the acquisition unit is configured to
select the imaging position correction application recommended to be actually introduced from the plurality of imaging position correction applications, based on at least one of comparison between the number of times each of the plurality of imaging position correction applications was used and a predetermined threshold of the number of times and a ranking of the plurality of imaging position correction applications based on the number of times each of the plurality of imaging position correction application was used; and
acquire the recommendation information including information on the selected imaging position correction application recommended to be actually introduced.

(Item 6)
The imaging position correction application introduction support system as recited in any one of the above-described Items 2 to 5,
wherein the storage unit stores, as the tentative use information, at least the degree of correction when the relative position of the X-ray irradiation unit with respect to the specific site of the subject was corrected by the imaging position correction application, and
wherein the acquisition unit is configured to
select the imaging position correction application recommended to be actually introduced, from the plurality of imaging position correction applications, based on the degree of correction when the relative position of the X-ray irradiation unit with respect to the specific site of the subject by the imaging position correction application was corrected and a predetermined threshold of the degree of correction, the degree of correction and the predetermined threshold being stored in the storage unit as the tentative use information, and
acquire the recommendation information including the information on the selected imaging position correction application recommended to be actually introduced.

(Item 7)
The imaging position correction application introduction support system as recited in any one of the above-described Items 2 to 6,
wherein the imaging position correction application to be introduced includes a knee imaging position correction application for correcting a relative position of the X-ray irradiation unit with respect to a knee of the subject when capturing an X-ray image of the knee of the subject,
wherein the storage unit stores, as the tentative use information, at least one of the number of times the knee imaging position correction application was used and a degree of correction when a relative position of the X-ray irradiation unit with respect to the knee of the subject was corrected, and
wherein the acquisition unit is configured to determine the knee imaging position correction application as the imaging position correction application recommended to be actually introduced, based on at least one of magnitude of the number of times the knee imaging position correction application was used, the magnitude of the number of times being stored in the storage unit as the tentative use information, and magnitude of a degree of correction when the relative position of the X-ray irradiation unit with respect to the knee of the subject was corrected by the knee imaging position correction application, the degree of correction being stored in the storage unit as the tentative use information.

(Item 8)
The imaging position correction application introduction support system as recited in any one of the above-described Items 2 to 7, further comprising:
a server connected to an X-ray imaging apparatus in which the imaging position correction application is tentatively introduced, the X-ray imaging apparatus being configured to capture an X-ray image of the subject via a network,
wherein the server includes a storage unit and an acquisition unit, and
wherein the server is configured to
cause the storage unit to store, via a network, the tentative use information acquired from the X-ray imaging apparatus, and
acquire the recommendation information for recommending an introduction of the imaging position correction application to a user, based on the tentative use information stored in the storage unit.

(Item 9)
The imaging position correction application introduction support system as recited in any one of the above-described Items 2 to 7, further comprising:
an X-ray imaging apparatus in which the imaging position correction application is tentatively introduced, the X-ray imaging apparatus being configured to capture an X-ray image of the subject,
wherein the X-ray imaging apparatus includes:
the X-ray irradiation unit;
the storage unit;
the display unit;
an X-ray detection unit configured to detect X-rays emitted from the X-ray irradiation unit and transmitted through the subject; and
a processing unit as the acquisition unit, the processing unit being configured to process the imaging position correction application and acquire the recommendation information, and
wherein the processing unit of the X-ray imaging apparatus is configured to
cause the storage unit to store the tentative use information,
acquire the recommendation information for recommending an actual introduction of the imaging position correction application to a user, based on the tentative use information stored in the storage unit, and
cause the display unit to display the acquired recommendation information.

(Item 10)
An imaging position correction application introduction support method, comprising:
a storage step configured to cause the storage unit to store tentative use information on when an imaging position correction application was tentatively used, as information to be used to recommend an actual introduction of the imaging position correction application tentatively introduced as an application for correcting a relative position of an X-ray irradiation unit for emitting X-rays with respect to a specific site of a subject when capturing an X-ray image of the specific site of the subject; and
a display step configured to display information based on the tentative use information stored in the storage unit;

wherein the storage step includes a step configured to cause the storage to store, as the tentative use information, at least one of the number of times the imaging position correction application was used and a degree of correction when the relative position of the X-ray irradiation unit with respect to the specific site of the subject was corrected by the imaging position correction application.

The invention claimed is:

1. An imaging position correction application introduction support system, comprising:
a storage unit configured to store tentative use information on when an imaging position correction application was tentatively used, as information to be used to recommend an actual introduction of the imaging position correction application tentatively used as an application for correcting a relative position of an X-ray irradiation unit for emitting X-rays with respect to a specific site of a subject when capturing an X-ray image of the specific site of the subject; and
a display unit configured to display information based on the tentative use information stored in the storage unit,
wherein the storage unit is configured to store, as the tentative use information, at least one of a number of times the imaging position correction application was used and a degree of correction when the relative position of the X-ray irradiation unit with respect to the specific site of the subject was corrected by the imaging position correction application.

2. The imaging position correction application introduction support system as recited claim 1, further comprising:
an acquisition unit configured to acquire, as the information to be used to recommend the actual introduction of the imaging position correction application to a user, recommendation information including information on the imaging position correction application recommended to be actually introduced, based on the tentative use information,
wherein the display unit is configured to display the recommendation information as information based on the tentative use information.

3. The imaging position correction application introduction support system as recited in claim 2,
wherein the acquisition unit is configured to
determine the imaging position correction application recommended to be actually introduced, based on at least one of magnitude of the number of times the imaging position correction application was used, the magnitude of the number of times being stored in the storage unit as the tentative use information, and magnitude of a degree of correction when the relative position of the X-ray irradiation unit with respect to the specific site of the subject was corrected by the imaging position correction application, the degree of correction being stored in the storage unit as the tentative use information, and
acquire the recommendation information including information on the determined imaging position correction application recommended to be actually introduced.

4. The imaging position correction application introduction support system as recited in claim 3,
wherein the storage unit stores at least the number of times the imaging position correction application was used as the tentative use information, and
wherein the acquisition unit is configured to
select the imaging position correction application recommended to be actually introduced from a plurality of imaging position correction applications, based on the magnitude of the number of times the imaging position correction application was used, the number of times being stored in the storage unit as the tentative use information, and
acquire the recommendation information including information on the selected imaging position correction application recommended to be actually introduced.

5. The imaging position correction application introduction support system as recited in claim 4,
wherein the acquisition unit is configured to
select the imaging position correction application recommended to be actually introduced from the plurality of imaging position correction applications, based on at least one of comparison between the number of times each of the plurality of imaging position correction applications was used and a predetermined threshold of the number of times and a ranking of the plurality of imaging position correction applications based on the number of times each of the plurality of imaging position correction application was used; and
acquire the recommendation information including information on the selected imaging position correction application recommended to be actually introduced.

6. The imaging position correction application introduction support system as recited in claim 2,
wherein the storage unit stores, as the tentative use information, at least the degree of correction when the relative position of the X-ray irradiation unit with respect to the specific site of the subject was corrected by the imaging position correction application, and
wherein the acquisition unit is configured to
select the imaging position correction application recommended to be actually introduced, from the plurality of imaging position correction applications, based on the degree of correction when the relative position of the X-ray irradiation unit with respect to the specific site of the subject by the imaging position correction application was corrected and a predetermined threshold of the degree of correction, the correction degree and the predetermined threshold being stored in the storage unit as the tentative use information, and
acquire the recommendation information including the information on the selected imaging position correction application recommended to be actually introduced.

7. The imaging position correction application introduction support system as recited in claim 2,
wherein the imaging position correction application to be introduced includes a knee imaging position correction application for correcting a relative position of the X-ray irradiation unit with respect to a knee of the subject when capturing an X-ray image of the knee of the subject,
wherein the storage unit stores, as the tentative use information, at least one of the number of times the knee imaging position correction application was used and a degree of correction when a relative position of the X-ray irradiation unit with respect to the knee of the subject was corrected, and
wherein the acquisition unit is configured to determine the knee imaging position correction application as the imaging position correction application recommended to be actually introduced, based on at least one of magnitude of the number of times the knee imaging position correction application was used, the magnitude of the number of times being stored in the storage unit as the tentative use information, and magnitude of a degree of correction when the relative position of the X-ray irradiation unit with respect to the knee of the subject was corrected by the knee imaging position correction application, the degree of correction being stored in the storage unit as the tentative use information.

8. The imaging position correction application introduction support system as recited in claim 2, further comprising:

a server connected to an X-ray imaging apparatus in which the imaging position correction application is tentatively introduced, the X-ray imaging apparatus being configured to capture an X-ray image of the subject via a network, wherein the server includes a storage unit and an acquisition unit, and wherein the server is configured to cause the storage unit to store, via a network, the tentative use information acquired from the X-ray imaging apparatus, and acquire the recommendation information for recommending an introduction of the imaging position correction application to a user, based on the tentative use information stored in the storage unit.

9. The imaging position correction application introduction support system as recited in claim 2, further comprising:

an X-ray imaging apparatus in which the imaging position correction application is tentatively introduced, the X-ray imaging apparatus being configured to capture the X-ray image of the subject, wherein the X-ray imaging apparatus includes:

the X-ray irradiation unit;

the storage unit;

the display unit;

an X-ray detection unit configured to detect X-rays emitted from the X-ray irradiation unit and transmitted through the subject; and a processing unit as the acquisition unit, the processing unit being configured to process the imaging position correction application and acquire the recommendation information, and wherein the processing unit of the X-ray imaging apparatus is configured to cause the storage unit to store the tentative use information, acquire the recommendation information for recommending an actual introduction of the imaging position correction application to a user, based on the tentative use information stored in the storage unit, and cause the display unit to display the acquired recommendation information.

10. An imaging position correction application introduction support method, comprising:

a storage step configured to cause the storage unit to store tentative use information on when an imaging position correction application was tentatively used, as information to be used to recommend an actual introduction of the imaging position correction application tentatively introduced as an application for correcting a relative position of an X-ray irradiation unit for emitting X-rays with respect to a specific site of a subject when capturing an X-ray image of the specific site of the subject; and a display step configured to display information based on the tentative use information stored in the storage unit;

wherein the storage step includes a step configured to cause the storage to store, as the tentative use information, at least one of the number of times the imaging position correction application was used and a degree of correction when the relative position of the X-ray irradiation unit with respect to the specific site of the subject was corrected by the imaging position correction application.

* * * * *